US010543579B2

(12) United States Patent
Zhou et al.

(10) Patent No.: US 10,543,579 B2
(45) Date of Patent: Jan. 28, 2020

(54) POLISHING APPARATUSES AND POLISHING METHODS

(71) Applicant: Micron Technology, Inc., Boise, ID (US)

(72) Inventors: Jian Zhou, Boise, ID (US); Hongqi Li, Boise, ID (US); James A. Cultra, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 16/375,685

(22) Filed: Apr. 4, 2019

(65) Prior Publication Data

US 2019/0232457 A1   Aug. 1, 2019

Related U.S. Application Data

(62) Division of application No. 15/671,895, filed on Aug. 8, 2017, now Pat. No. 10,286,517.

(51) Int. Cl.
*B24B 37/013* (2012.01)
*B24B 37/04* (2012.01)
(Continued)

(52) U.S. Cl.
CPC .......... *B24B 37/013* (2013.01); *B24B 37/042* (2013.01); *B24B 37/105* (2013.01);
(Continued)

(58) Field of Classification Search
CPC ... B24B 37/013; B24B 37/042; B24B 37/105; B24B 49/10; B24B 57/02; H01L 21/3103; H01L 21/30625; H01L 22/26
See application file for complete search history.

(56) References Cited

U.S. PATENT DOCUMENTS 5,433,651 A * 7/1995 Lustig .................. B24B 37/013
216/88
6,045,434 A 4/2000 Fisher et al.
(Continued)

FOREIGN PATENT DOCUMENTS

KR  10-1999-0044998   6/1999
TW       383253        3/2000
(Continued)

OTHER PUBLICATIONS

WO PCT/US2018/041678 Search Rept., dated Dec. 7, 2018, Micron Technology, Inc.
(Continued)

*Primary Examiner* — Fernando L Toledo
*Assistant Examiner* — Neil R Prasad
(74) *Attorney, Agent, or Firm* — Wells St. John P.S.

(57) ABSTRACT

Some embodiments include an apparatus having a polishing mechanism configured to polish a surface of a wafer. The polishing mechanism converts fresh slurry to used slurry during a polishing process. At least one emitter is configured to direct electromagnetic radiation onto or through the used slurry. At least one detector is configured to detect transmittance of the electromagnetic radiation through the used slurry or reflection of the electromagnetic radiation from the used slurry. An identification system is coupled with the at least one detector and is configured to identify a property of the used slurry indicating that an endpoint of the polishing process has been reached. Control circuitry is coupled with the identification system and is configured to stop the polishing process based on receiving a trigger from the identification system. Some embodiments include polishing methods.

20 Claims, 14 Drawing Sheets

(51) Int. Cl.
*B24B 37/10* (2012.01)
*B24B 49/10* (2006.01)
*B24B 57/02* (2006.01)
*G01N 21/31* (2006.01)
*H01L 21/306* (2006.01)
*H01L 21/66* (2006.01)

(52) U.S. Cl.
CPC .............. *B24B 49/10* (2013.01); *B24B 57/02* (2013.01); *G01N 21/3103* (2013.01); *H01L 21/30625* (2013.01); *H01L 22/26* (2013.01)

(56) References Cited

U.S. PATENT DOCUMENTS

| | | |
|---|---|---|
| 6,183,656 B1 | 2/2001 | Ide et al. |
| 7,226,339 B2 | 6/2007 | Benvegnu et al. |
| 8,460,507 B2 | 6/2013 | Spiro et al. |
| 2002/0171837 A1 | 11/2002 | Cheng |
| 2003/0213558 A1 | 11/2003 | Basol et al. |
| 2003/0232576 A1 | 12/2003 | Kimura et al. |
| 2005/0061674 A1* | 3/2005 | Wang ............ B23H 5/06 205/78 |
| 2005/0064802 A1* | 3/2005 | Wiswesser ...... B24B 37/013 451/285 |
| 2005/0205521 A1* | 9/2005 | Kume ............ H01L 21/31111 216/87 |
| 2007/0218806 A1* | 9/2007 | Kistler ............ B24B 37/013 451/5 |
| 2010/0187200 A1 | 7/2010 | Spiro et al. |

FOREIGN PATENT DOCUMENTS

| | | |
|---|---|---|
| TW | 393381 | 6/2000 |
| TW | 490755 | 6/2002 |
| TW | 200717637 | 5/2007 |
| TW | 200916261 | 4/2009 |

OTHER PUBLICATIONS

WO PCT/US2018/041678 Writ. Opin., dated Dec. 7, 2018, Micron Technology, Inc.

Gokhale et al., "Infrared Absorption Properties of Carbon Nanotube/ Nanodiamond Based Thin Film Coatings", IEEE Journal of Microelectromechanical Systems, 2013, United States, pp. 1-7.

Schwan et al., "Raman Spectroscopy on Amorphous Carbon Films", Journal of Applied Physics vol. 80(1), Jul. 1, 1996, United States, pp. 440-442.

TW TW 107125980 SR Translation, dated May 16, 2019, Micron Technology, Inc.

* cited by examiner

POLISHING APPARATUSES AND POLISHING METHODS

RELATED PATENT DATA

This patent resulted from a divisional of U.S. patent application Ser. No. 15/671,895, filed Aug. 8, 2017, which is hereby incorporated by reference herein.

TECHNICAL FIELD

Polishing apparatuses and polishing methods; such as apparatuses and methods for chemical-mechanical polishing of semiconductor substrates (e.g., silicon-containing wafers).

BACKGROUND

Chemical-mechanical polishing (CMP) may be utilized to remove material during the fabrication of semiconductor devices (e.g., integrated circuitry). An example CMP process is described with reference to FIG. 1. Specifically, a construction 10 comprises an upper structure 12 over a supporting base 14. The construction 10 is subjected to CMP to remove the upper structure 12, and to leave the base 14 with a planarized surface 15 thereover.

The structure 12 may comprise a single material, or may comprise multiple materials; and in some embodiments may be referred to as a mass, layer, etc.

The base 14 may be a semiconductor substrate. The term "semiconductor substrate" means any construction comprising semiconductive material (e.g., silicon, germanium, etc.), including, but not limited to, bulk semiconductive materials such as a semiconductive wafer (either alone or in assemblies comprising other materials), and semiconductive material layers (either alone or in assemblies comprising other materials). The term "substrate" refers to any supporting structure, including, but not limited to, the semiconductor substrates described above. In some applications, the base 14 may correspond to a semiconductor substrate containing one or more materials associated with integrated circuit fabrication. Such materials may include, for example, one or more of refractory metal materials, barrier materials, diffusion materials, insulator materials, etc.

A difficulty which may occur during CMP is associated with determining an endpoint of the CMP process. Specifically, it may be desired to stop the CMP process quickly after the entirety of the upper structure 12 is removed, and before removing any significant amount of the base 14. If the base 14 comprises relatively hard material as compared to the upper structure 12, the endpoint of the CMP process may be ascertained by a change in friction. However, if the base 14 comprises soft material, it may be more difficult to ascertain the endpoint of the CMP process. Further, the soft material may be detrimentally deformed during the CMP process if too much pressure is applied to the soft material, resulting in dishing and/or other undesired attributes.

In some aspects, the base 14 may comprise a heterogeneous upper surface. For instance, FIG. 2 shows an example base 14 corresponding to a semiconductor wafer. A region of the surface 15 of base 14 is shown in expanded view, and such region includes multiple materials 16, 18 and 20. In some applications, the material 16 may be a relatively hard material (e.g., may comprise, consist essentially of, or consist of carbon), and the materials 18 and 20 may be relatively soft material. For instance, the material 18 may comprise silicon, oxygen and carbon; such as, for example, material deposited utilizing spin-on methodology. The material 20 may comprise, consist essentially of, or consist of silicon dioxide; and in some cases may correspond to low-density silicon dioxide. In some particular applications, the base 14 of FIG. 2 may correspond to a construction utilized during fabrication of three-dimensional cross-point integrated circuit architecture.

A difficulty in utilizing CMP to expose the upper surface 15 of the construction 10 of FIG. 2 is that the softer materials 18 and 20 may be deformed if too much pressure is utilized during the CMP and/or if the CMP is not stopped promptly upon reaching the desired endpoint (i.e., upon the initial exposure of upper surface 15). Accordingly, it would be desirable to develop improved methods of CMP.

A prior art CMP apparatus 30 is described with reference to FIGS. 3 and 3A. The apparatus 30 includes a platen (i.e., table) 32 coupled with a first shaft 34, and configured to spin (with the spinning being represented by an arrow 33). The apparatus also includes a wafer holder (i.e., carrier) 36, coupled with a second shaft 38, and configured to spin (with the spinning being represented by an arrow 35). Also, the wafer holder is configured to sweep laterally across an upper surface of the platen 32 (with the sweeping being represented with arrows 37). A wafer 10 is shown to be retained within the wafer holder 36. The wafer 10 has a surface 11 facing the platen 32, with such surface being polished during the polishing (i.e., CMP) process.

The movements of the platen 32 and wafer holder 36 are controlled utilizing a controller 40. Such controller may also control a downforce on the wafer holder 36 during a polishing process. The downforce is a vertical force on the wafer holder 36 which presses the wafer 10 toward an upper surface of the platen 32, and corresponds to a vertical force on the surface 11 of the wafer 10 during the polishing process.

The apparatus 30 includes a dispenser 40 which dispenses slurry 42 onto the platen 32. The dispenser 40 may be considered to be part of a slurry-dispensing mechanism, and is in fluid indication with a reservoir (not shown) containing the slurry.

The slurry 42 forms a film 44 across an upper surface of the platen 32, with such film extending to under the wafer 10. The slurry 42 is initially a fresh slurry as it is dispensed onto the upper surface of platen 32, but becomes a used slurry after it is utilized for polishing the surface 11 of wafer 10. The used slurry will carry materials removed from wafer 10. The used slurry is expelled outwardly through centrifugal force, with the outward movement of the slurry being indicated with arrows 43.

A shield 46 surrounds a lateral periphery of the platen 32, and is configured to block laterally expelled used slurry during the polishing process.

A basin 48 collects the used slurry. The basin 48 comprises outlets 50, and the slurry exits the basin through the outlets 50. The illustrated basin 48 is shown to comprise a pair of the outlets 50 along the cross-sectional view of FIG. 3. The basin may comprise more than two outlets in some applications, or may comprise only a single outlet.

In some applications, an endpoint of a CMP process is determined by a change in friction along the surface 11 of wafer 10 due to a change in the materials exposed along such surface. The change in friction may be detected by the controller 40 as a change in the power required to maintain a particular spinning rate of platen 32. The CMP apparatus 30 of FIGS. 3 and 3A may be effective in applications in which the endpoint of the CMP process may be determined by the change in friction.

In some applications, the endpoint of a CMP process cannot be readily determined simply by a change in friction along the surface 11 of wafer 10. For instance, if the downforce on wafer 10 is relatively light (i.e., less than or equal to about 1 pound per square inch (psi) during the polishing process), the change in friction may be difficult to detect. Further, a reason for utilizing a relatively light downforce is because a final polished surface of wafer 10 will comprise soft materials (with example soft materials being the silicon dioxide materials described above with reference to FIG. 2), and polishing beyond the desired endpoint may be particularly problematic relative to soft materials (as discussed above with reference to FIGS. 1 and 2). Accordingly, it would be desirable to develop improved apparatuses for utilization in CMP applications in which frictional changes are not suitable for determining the endpoint of a polishing process, and to develop improved methods for CMP.

DETAILED DESCRIPTION OF THE ILLUSTRATED EMBODIMENTS

Some embodiments include CMP apparatuses configured to incorporate spectroscopic analysis of used slurry to ascertain an endpoint of a polishing process. Example embodiments are described with reference to FIGS. 4-11.

Figure 4:
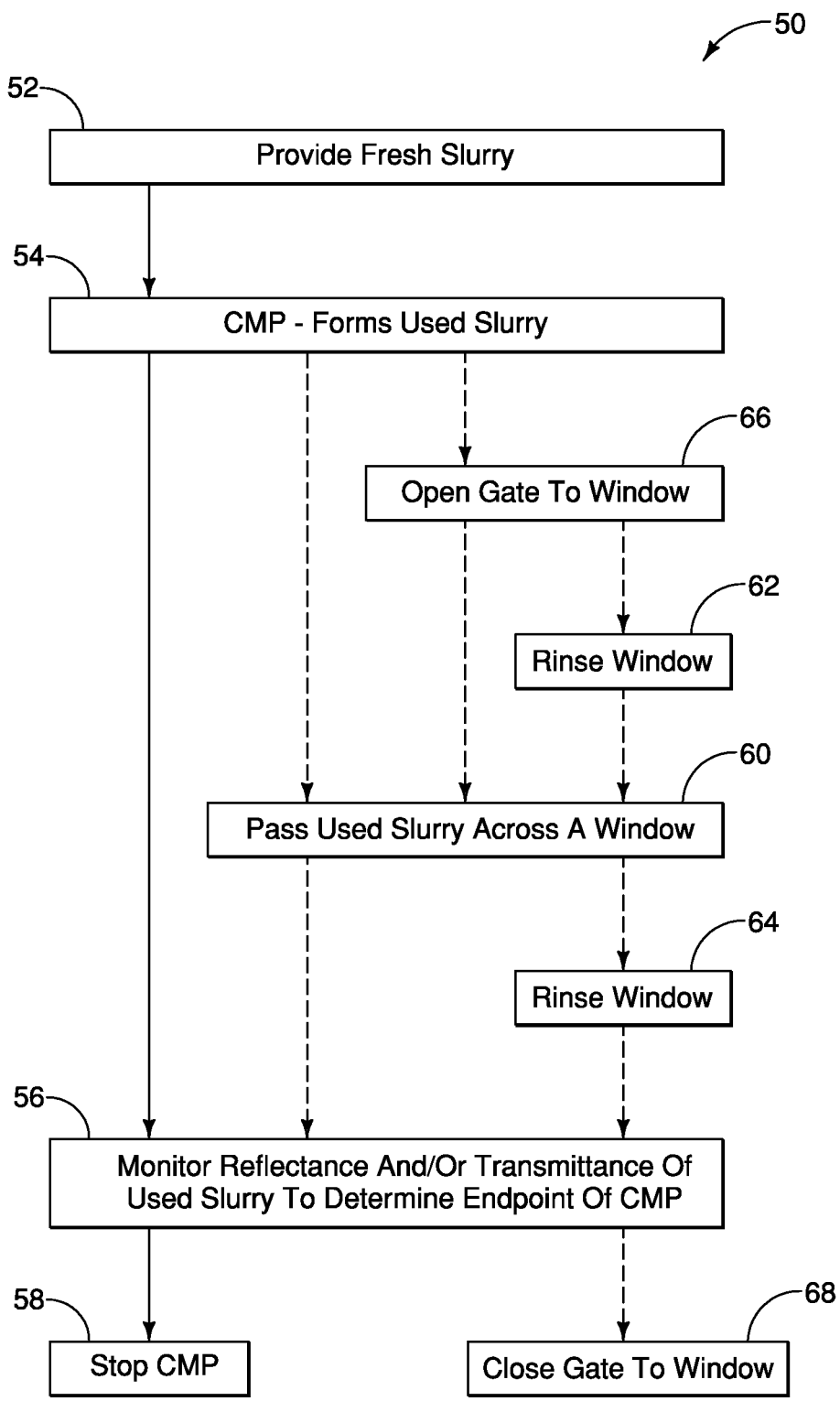
FIG. 4 is a flow chart diagram describing an example embodiment polishing processes.

Referring to FIG. 4, a flowchart 50 is utilized to explain some embodiments of example polishing processes of the present invention.

Figure 3:
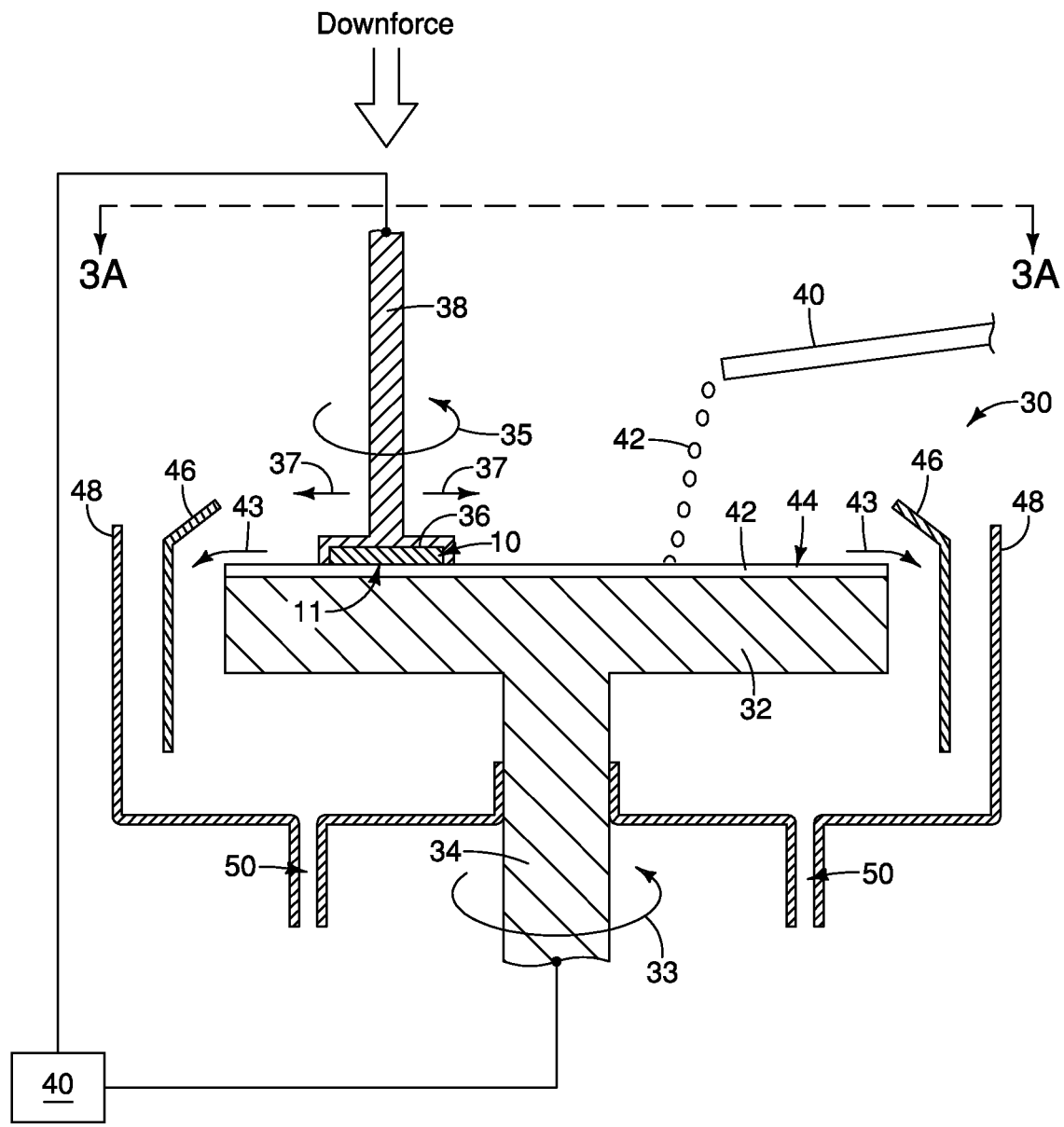
FIGS. 3 and 3A are a diagrammatic cross-sectional side view and a diagrammatic partially-sectional top view of a prior art polishing apparatus.

In an initial step 52, fresh slurry is provided. In some applications, the fresh slurry may be provided by utilizing a dispenser 40 of the type described above with reference to FIG. 3.

The slurry is utilized for CMP at step 54, which forms used slurry.

Reflectance from the used slurry and/or transmittance through the used slurry is monitored at step 56 to determine an endpoint of the CMP.

Once the endpoint is determined, the CMP process is stopped at step 58.

A series of optional steps are illustrated, with dashed arrows being provided to and from the optional steps to emphasize that the steps are optional.

An optional step 60 comprises passing the used slurry across a window. The reflectance and/or transmittance may be determined while the slurry is passing across the window.

Optional steps 62 and 64 comprise rinsing the window prior to passing the used slurry across the window, and/or after passing the used slurry across the window. The rinsing of the window may improve spectroscopic examination of the used slurry passing across the window.

Optional steps 66 and 68 include opening a gate to the window and closing the gate, respectively. The utilization of the gate may enable the flow of the used slurry across the window to be controlled so that the used slurry is only flowing across the window during a short duration in which an endpoint is expected, rather than during the entire duration of a polishing process. Such may help to keep the window clean, and may thereby improve spectroscopic examination of the used slurry passing across the window.

Figure 3A:
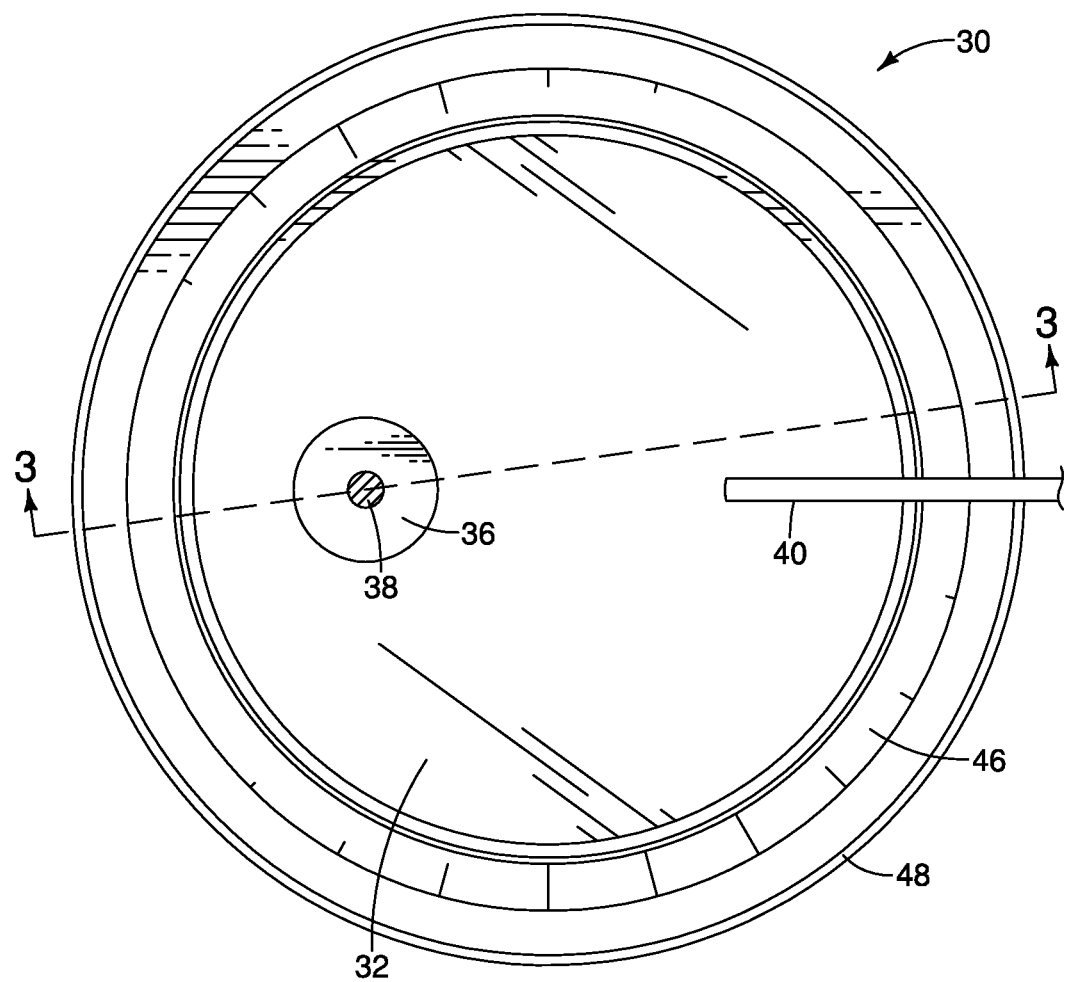
Figure 5:
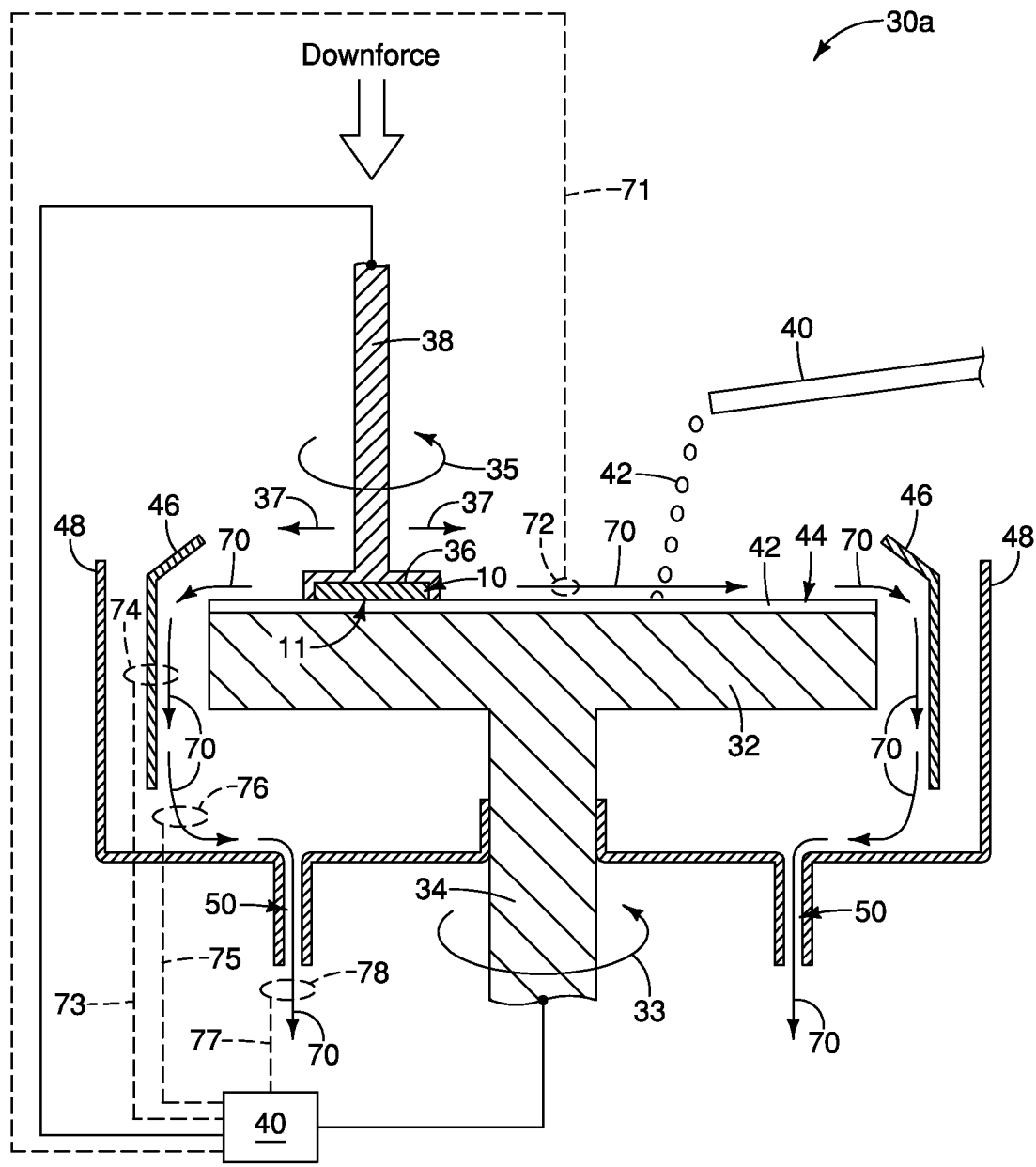
FIG. 5 is a diagrammatic cross-sectional side view of an example embodiment polishing apparatus.

Referring to FIG. 5, an example apparatus 30a is illustrated. The apparatus 30a is based on the prior art apparatus 30 described above with reference to FIGS. 3 and 3A; but contains enhancements for detecting the endpoint of a CMP process, and then terminating the CMP process based on detection of the endpoint. The CMP process may be ceased immediately upon detection of the endpoint, or may be ceased after a programmed delay.

The apparatus 30a includes the platen 32, shaft 34, wafer holder 36, shaft 38, shield 46 and basin 48 described above with reference to FIGS. 3 and 3A. The apparatus 30a also comprises the controller 40 utilized for controlling the downforce on the wafer holder 36, and for controlling the relative motion of the wafer holder 36 relative to the platen 32.

The slurry 42 is shown along an upper surface of the platen 32, with such slurry forming the film 44. The used slurry is ejected toward shield 46 through centrifugal force, and then falls into the basin 48. The used slurry exits the basin 48 through the outlets (i.e., drains) 50. The used slurry is diagrammatically illustrated with arrows 70, with such arrows also showing approximate paths of the ejected slurry.

The downforce utilized during operation of the apparatus 30a may be less than or equal to about 1 pound per square inch (psi); and in some embodiments may be within a range of from about 0.1 psi to less than or equal to about 1 psi.

Figure 1:
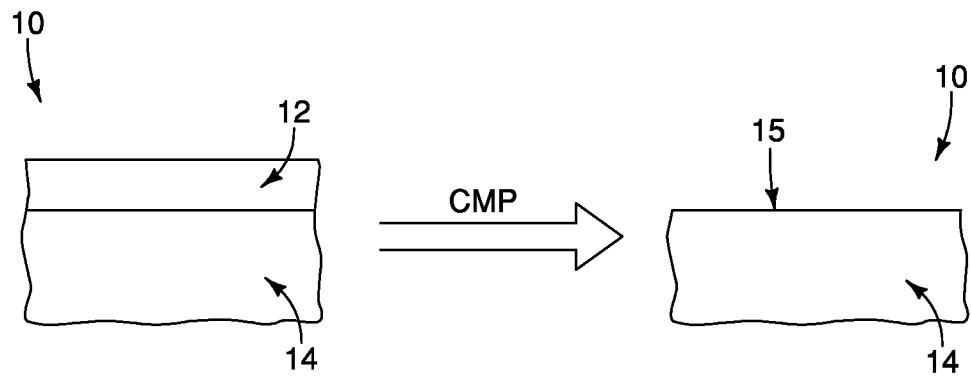
FIG. 1 is a diagrammatic cross-sectional side view of a semiconductor wafer subjected to a prior art chemical-mechanical polishing (CMP) process.
Figure 2:
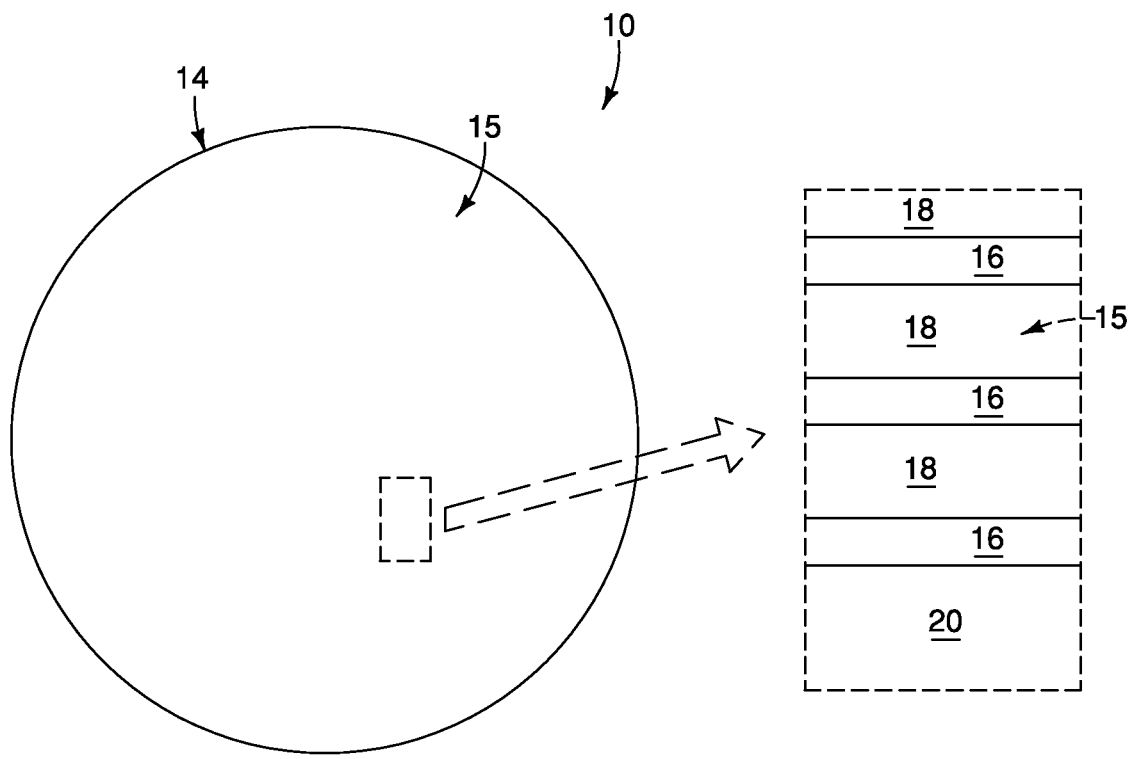
FIG. 2 is a diagrammatic top view of the polished prior art semiconductor wafer of FIG. 1, and shows an expanded region of the polished semiconductor wafer.

The apparatus 30a includes one or more systems for spectroscopically analyzing the used slurry to ascertain if the used slurry has a predetermined property indicative of the endpoint of the polishing process. An example polishing process was described above in the Background section as removing a structure 12 from over a base 14 (FIG. 1). In some applications, the base 14 may comprise a constituent which is not present in the structure 12. Accordingly, the predetermined property indicative of the endpoint of the polishing process may be the presence of such constituent within the used slurry. For instance, in some applications the structure 12 may comprise, consist essentially of, or consist of silicon nitride; and have little or no carbon therein. The base 14 may have an upper surface comprising one or more carbon-containing materials, and the predetermined property indicative of the endpoint of the polishing process may be the presence of carbon within the used slurry. In other applications, the constituent present in the base 14 and absent from the structure 12 may be metal (e.g., titanium, tungsten, platinum, rhodium, etc.), metal-containing material (e.g., metal carbide, metal nitride, metal silicide, etc.), or any other substance which may be spectroscopically detected in the used slurry.

In some applications, the structure 12 and the base 14 may both comprise a common constituent, but the concentration of the constituent may be substantially different at an upper surface of the base 14 than within the structure 12. Accordingly, the predetermined property indicative of the endpoint of the polishing process may correspond to a threshold concentration of the constituent within the used slurry. For instance, both the structure 12 and the base 14 may comprise carbon, but the upper surface of the base 14 may comprise a substantially higher concentration of the carbon than does the structure 12. Accordingly, the predetermined property indicative of the endpoint of the polishing process may correspond to an upward spike in the carbon concentration within the used slurry. The process could also work if the base 14 has a lower concentration of carbon than the structure 12, with the predetermined property indicative of the endpoint of the polishing process being a downward spike in the carbon concentration. However, there may be a longer lag in determination of a downward spike in carbon concentration as compared to the determination of an upward spike in carbon concentration in that the background carbon concentration within the used slurry may initially interfere with the detection of the downward spike in carbon concentration.

The spectroscopic analysis of the used slurry may occur at any suitable location within the apparatus 30a of FIG. 5. Example locations 72, 74, 76 and 78 are diagrammatically illustrated. The location 72 is along an upper surface of the platen 32, and the spectroscopic analysis conducted at such location may correspond to determination of the reflective properties of the used slurry. The location 74 is along the shield 46, and the spectroscopic analysis conducted at such location may correspond to determination of reflective properties of the used slurry and/or determination of transmissive properties of the used slurry (the transmissive properties of the used slurry are the inverse of absorptive properties of the used slurry, and may alternatively be referred to as absorptive properties). The location 76 is between the shield 46 and the basin 48, and the spectroscopic analysis conducted at such location may correspond to determination of reflective properties of the used slurry and/or determination of transmissive properties of the used slurry. The location 78 is downstream of the outlet 50, and the spectroscopic analysis conducted at such location may correspond to determination of reflective properties of the used slurry and/or determination of transmissive properties of the used slurry.

Spectroscopic analysis may be conducted at only one of the locations 72, 74, 76 and 78, or may be conducted at two or more of the locations 72, 74, 76 and 78. Also, the location 72 may be representative of many locations at which spectroscopic analysis is conducted relative to used slurry along the surface of the platen 32. Analogously, the location 74 may be representative of one of many locations at which spectroscopic analysis is conducted relative to used slurry flowing along the shield 46; the location 76 may be representative of one of many locations at which spectroscopic analysis is conducted relative to used slurry flowing from the shield 46 to the basin 48; and the location 78 may be representative of one of many locations at which spectroscopic analysis is conducted relative to used slurry flowing along a path downstream from an outlet 50.

Spectroscopic analysis at the spectroscopic locations 72, 74, 76 and 78 may be conducted utilizing a system comprising an emitter and a detector. The emitter directs electromagnetic radiation onto or through the used slurry, and the detector detects reflectance and/or transmittance of the used slurry to ascertain if the predetermined property is present which indicates the endpoint of the CMP process. The systems utilized for the spectroscopic analysis may be coupled with the controller 40 (as is diagrammatically illustrated using dashed lines 71, 73, 75 and 77). Once the predetermined property indicative of the endpoint of the CMP process is detected, a trigger may be sent to the controller 40 to stop the CMP process.

There will often be a lag time between the time that an endpoint of a polishing process is reached (e.g., the time that the surface 15 of FIG. 1 is exposed), and the time of detection of the property indicative of the endpoint of the CMP process. Such lag time may depend upon, among other things, a distance of the spectroscopic analysis from the wafer 10 (with closer distances possibly providing shorter lag times than longer distances), the percentage of the total used slurry subjected to analysis (with higher percentages enabling better signal-to-noise, and thus possibly reducing the lag time), and the sensitivity of a detection process for a particular property indicative of the endpoint of the CMP process (with higher sensitivity possibly leading to reduced lag time). Thus, it may be desirable to balance multiple factors in order to achieve desired short lag times. In some example embodiments, the lag time may be less than or equal to about five seconds, less than or equal to about two seconds, or within a range of from about 0.1 second to about five seconds. In some embodiments, the time that an endpoint of a polishing process is reached may be referred to as the time that that the polishing process generates the property indicative of the endpoint of the CMP process.

Specific arrangements for spectroscopic analysis at each of the locations 72, 74, 76 and 78 are described with reference to FIGS. 6-11.

Figure 6:
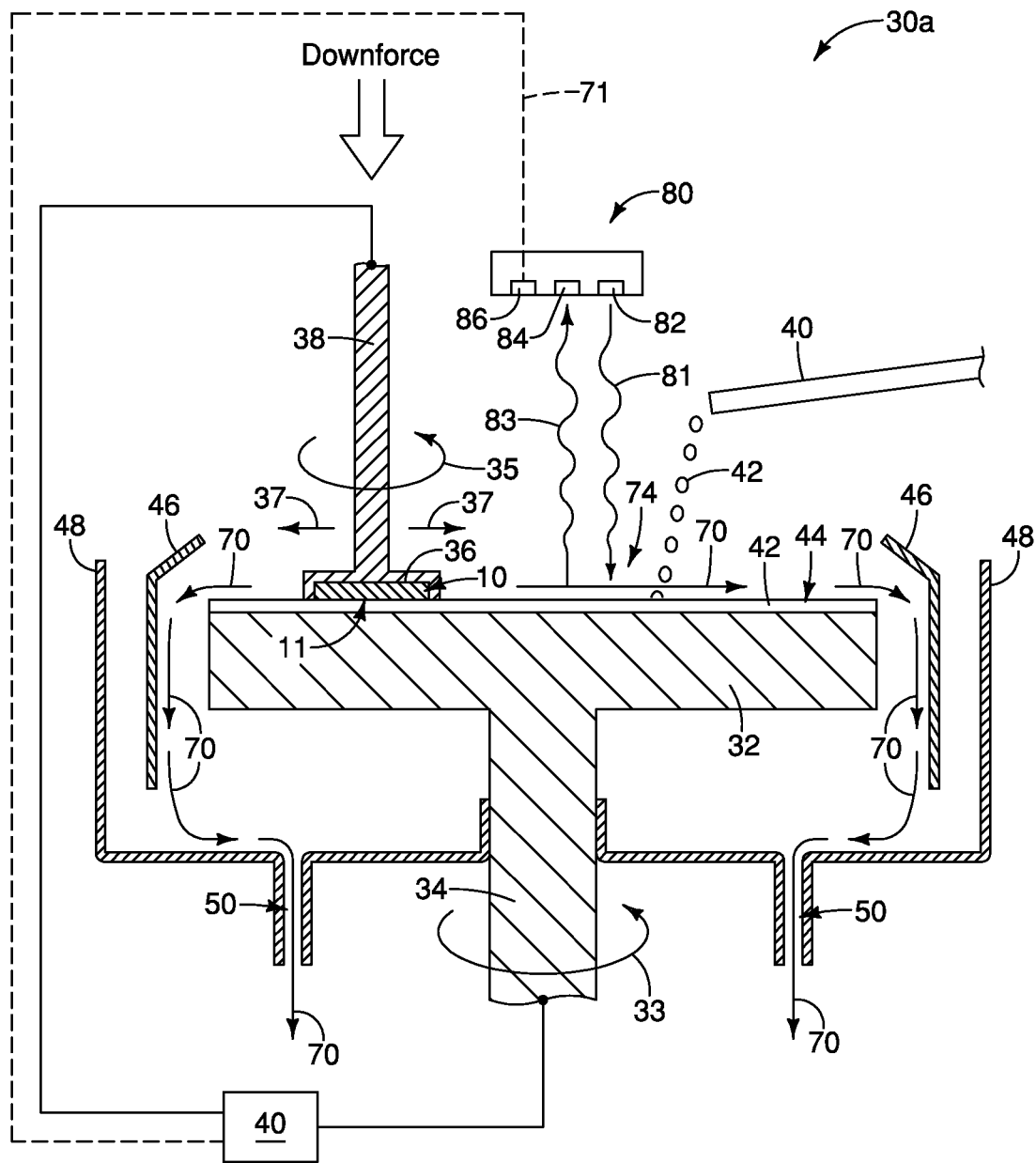
FIG. 6 is a diagrammatic cross-sectional side view of an example embodiment polishing apparatus.

Referring to FIG. 6, an example embodiment is shown in which spectroscopic analysis of the used slurry 70 is conducted at the location 74 along the upper surface of platen 32 utilizing a spectroscopic device 80. The device 80 includes an emitter 82 which directs electromagnetic radiation 81 onto the used slurry 70, and includes a detector 84 which detects electromagnetic radiation 83 reflected back from the used slurry 70. The device 80 also includes an identification system 86 coupled with the detector 84 and configured to identify the property of the used slurry indicating that an endpoint of the polishing process has been reached. Upon determining that such property is reached, the identification system 86 sends a trigger to the control circuitry 40 along the path 71. The control circuitry 40 is configured to stop the polishing process based on receiving the trigger from the identification system 86. The control circuitry 40 may be programmed to immediately stop the polishing process upon receiving the trigger from the identification system 86, or to stop the polishing process after a predetermined delay.

The emitted electromagnetic radiation 81 may comprise any suitable wavelength, and in some embodiments may have a wavelength within the ultraviolet range, the visible range or the infrared range. Similarly, the reflected electromagnetic radiation 83 may comprise any suitable wavelength, and in some embodiments may have a wavelength within the ultraviolet range, the visible range or the infrared range. In some embodiments, the spectroscopic device 80 may be configured to detect carbon, metal, and/or metal-containing material.

Although the spectroscopic device 80 is shown comprising a single emitter and a single detector, in other embodiments the device may comprise two or more emitters and/or may comprise two or more detectors. Also, although only a single spectroscopic device 80 is shown, in other embodiments there may be more than one spectroscopic device 80 utilized.

Figure 7:
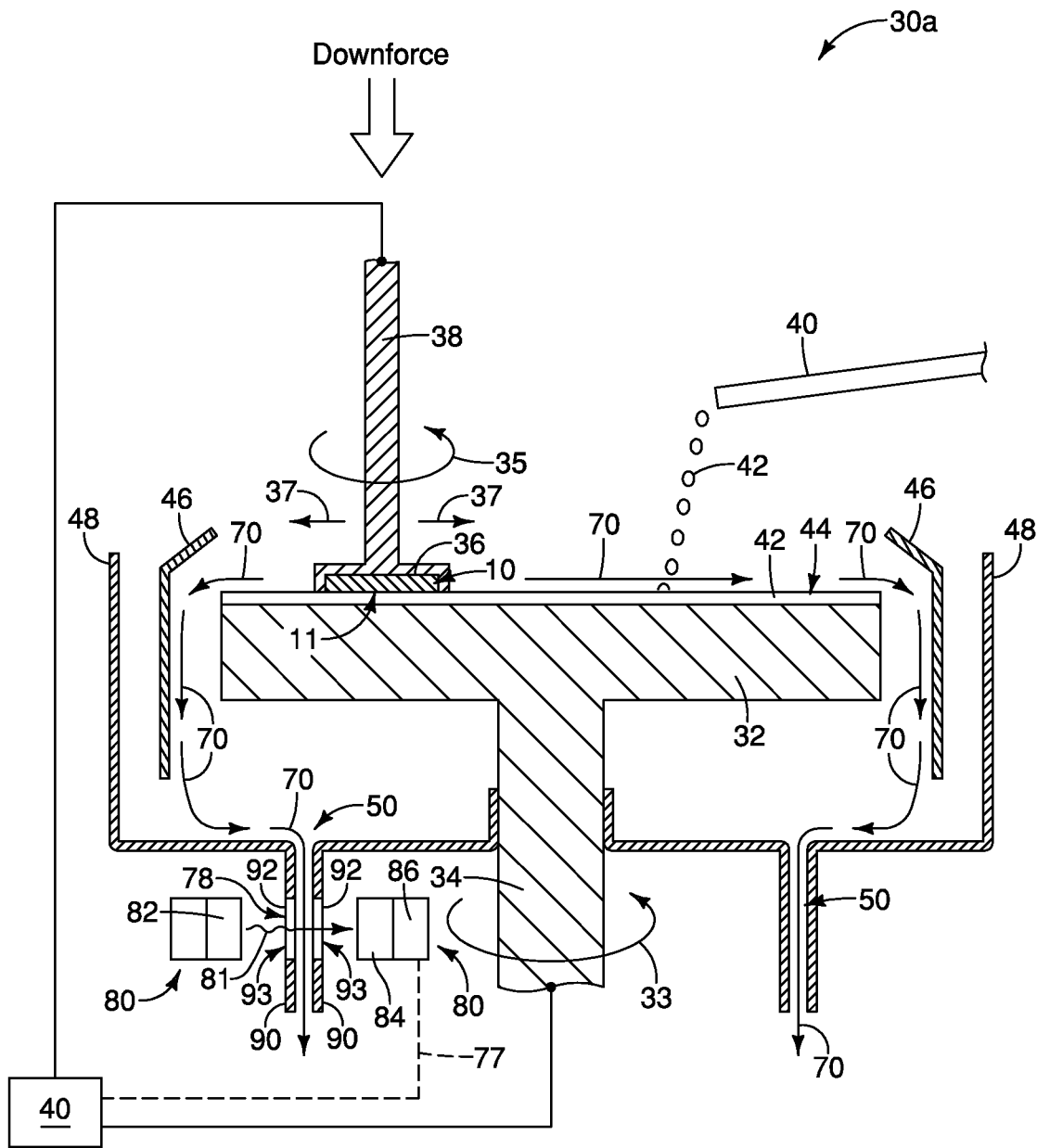
FIG. 7 is a diagrammatic cross-sectional side view of an example embodiment polishing apparatus.

Referring to FIG. 7, an example embodiment is shown in which spectroscopic analysis of the used slurry 70 is conducted at the location 78 downstream of the outlet 50 utilizing the spectroscopic device 80. Such location 78 may be referred to as a location along an outlet path in some embodiments. A tube 90 extends along the outlet path, and a window 92 is provided along such tube. The window 92 may comprise any suitable material transparent to the electromagnetic radiation which is passed through the window by the device 80; including, for example, plastic, glass, quartz, etc. In some embodiments, the window 92 may be considered to be configured as a conduit 93, with such conduit being downstream of the outlet 50 along the flow path of the used slurry 70.

The device 80 includes the emitter 82, and in FIG. 7 the emitter 82 is configured to direct the electromagnetic radiation 81 through the window 92 and through the used slurry 70. The device 80 also includes the detector 84, and in FIG. 7 the detector 84 detects electromagnetic radiation 81 which has passed through the used slurry 70. The detector 84 may determine transmittance (or conversely, absorbance) of the used slurry 70 relative to the electromagnetic radiation 81. The device 80 includes the identification system 86 coupled with the detector 84 and configured to identify the property of the used slurry indicating that an endpoint of the polishing process has been reached. Upon determining that such property is reached, the identification system 86 sends a trigger to the control circuitry 40 along the path 77. The control circuitry 40 is configured to stop the polishing process based on receiving the trigger from the identification system 86.

The emitted electromagnetic radiation 81 may comprise any suitable wavelength, and in some embodiments may have a wavelength within the ultraviolet range, the visible range or the infrared range. In some embodiments, the electromagnetic radiation may be infrared radiation utilized to detect carbon. In some embodiments, the spectroscopic device 80 may be configured to conduct Raman spectroscopy to detect carbon. In some embodiments, the spectroscopic device 80 may be configured to detect metal, and/or metal-containing material. In some embodiments, the device 80 of FIG. 7 may be configured to detect reflection from the used slurry 70 instead of, or in addition to, detecting transmittance.

Although the spectroscopic device 80 is shown comprising a single emitter and a single detector, in other embodiments the device may comprise two or more emitters and/or may comprise two or more detectors. Also, although only a single spectroscopic device 80 is shown, in other embodiments there may be more than one spectroscopic device 80 utilized. In the illustrated embodiment of FIG. 7, two outlets 50 are provided within the basin 48, and the window 92 is only provided downstream of one of the outlets. In other embodiments, the second outlet may be omitted so that all of the used slurry passes through the illustrated window 92. In yet other embodiments, multiple outlets may be utilized, and windows and spectroscopic devices may be provided downstream of two or more of such outlets.

Figure 7A:
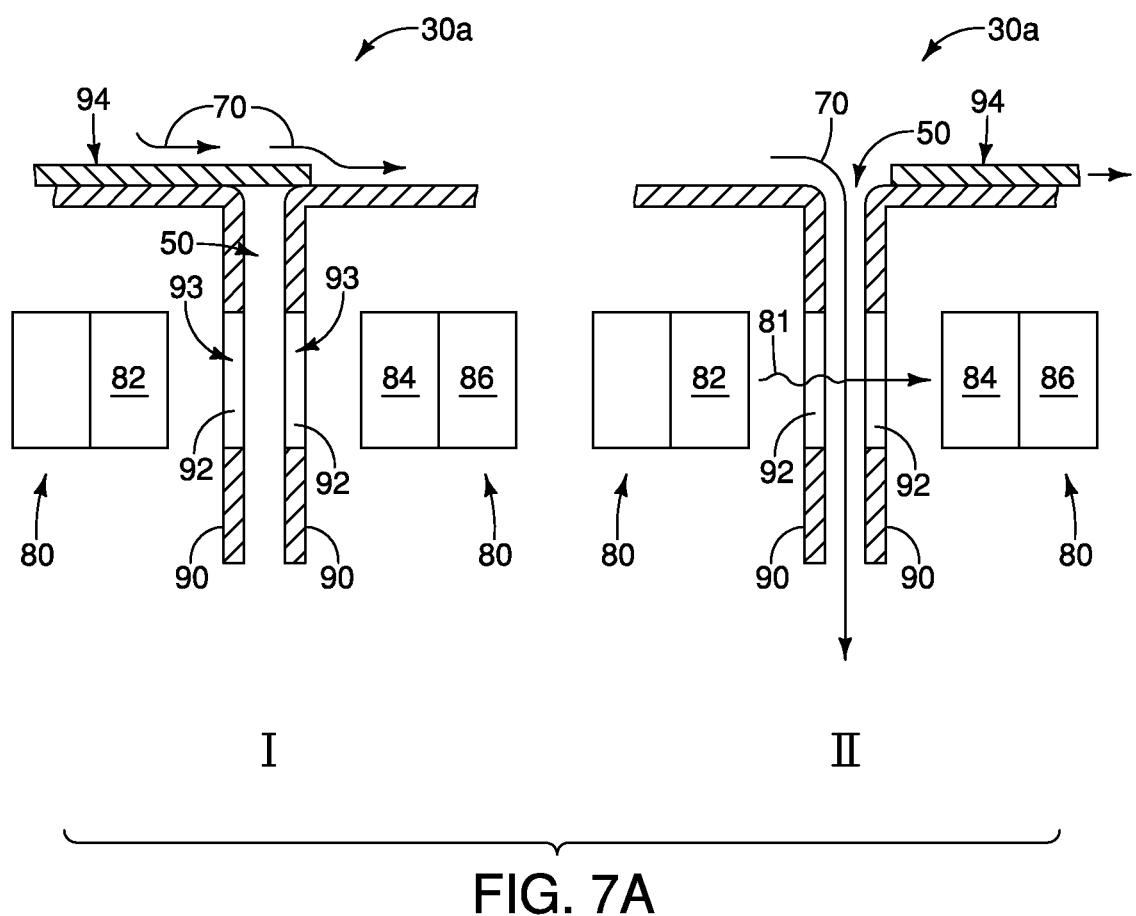
FIG. 7A is a diagrammatic cross-sectional side view of a region of the example embodiment polishing apparatus of FIG. 7 shown in two example operational modes.

An advantage of having more than one outlet in the basin is that the flow of used slurry through the outlet upstream of the window may be controlled so that the used slurry is only flowing across the window for a short duration of a polishing process, rather than for the entire polishing process. For instance, FIG. 7A shows an expanded region of construction 30a in accordance with an embodiment in which a gate 94 is provided to controllably block the flow of used slurry 70 through the outlet 50. In a first operational mode, I, the gate 94 blocks the outlet 50 (i.e., is in a "closed" position), and accordingly the used slurry 70 does not flow across the window 92. In a second operational mode, II, the gate 94 has been moved to open the outlet 50 (i.e., is in an "open" position) and such enables used slurry 70 to flow across the window 92. The transition from the first operational mode I to the second operation mode II is reversible, and in some embodiments may be controlled with the controller 40 (FIG. 7).

In some embodiments, an operator will have sufficient experience with a polishing process to know an approximate duration required to reach the endpoint. The gate 94 may be operated with controller 40 and utilized in the "closed" position to block the flow of used slurry 70 through the conduit 93 for a first period during the duration of the polishing process, before the endpoint of the polishing process is expected. Subsequently, the gate 94 may be moved to the "open" position for a second period which encompasses a time that the endpoint of the polishing process is expected. An advantage of keeping the gate 94 closed during at least some of the polishing process is that such may keep the window 92 relatively clean, as compared to embodiments in which the window is exposed to the used slurry during the entire duration of the polishing process. Another gate (i.e., a second gate), comparable to the gate 94 of FIG. 7A may be provided at another outlet of the basin (for instance, the second outlet shown in FIG. 7) and may be operated in an opposite manner relative to the gate over the conduit 93. Specifically, when used slurry is blocked from going through conduit 93, the used slurry can exit through the other outlet by having the second gate in an "open" position; and when it is desired to run the used slurry through conduit 93 (and thus across window 92), the other outlet may be blocked by having the second gate in the "closed" position.

In the illustrated embodiment of FIG. 7A, the emitter 82 only emits electromagnetic radiation 81 during the period in which gate 94 is in the "open" position, which may extend the lifetime of one or both of the emitter 82 and the detector 84. In other embodiments, the emitter 82 may emit radiation 81 continuously during the entire polishing process, including the period in which the gate 94 is in the "closed" position.

Figure 8:
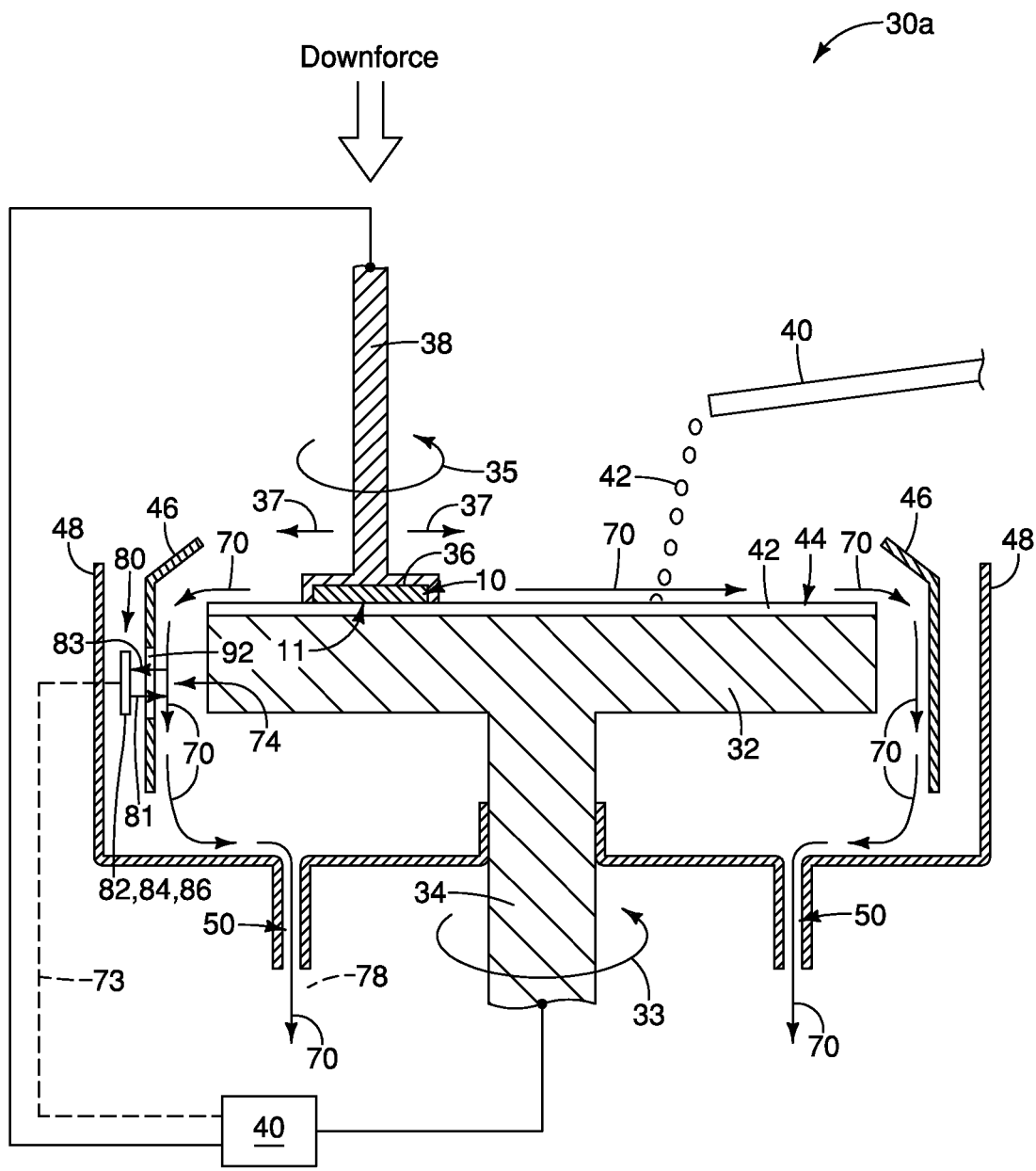
FIG. 8 is a diagrammatic cross-sectional side view of an example embodiment polishing apparatus.

Referring to FIG. 8, an example embodiment is shown in which spectroscopic analysis of the used slurry 70 is conducted at the location 74 along the shield 46 utilizing the spectroscopic device 80. A window 92 is provided along the shield 46. The window 92 may comprise any suitable material transparent to electromagnetic radiation being passed through the window. In the embodiment of FIG. 8, only a portion of the shield 46 comprises the transparent composition of window 92. In other embodiments, the entire shield 46 may comprise the transparent composition of window 92.

The device 80 includes the emitter 82, detector 84 and identification system 86. In the embodiment of FIG. 8, the device 80 is utilized to monitor reflectance of the used slurry passing by the window 92. The identification system 86 is coupled with the detector 84 and configured to identify the property of the used slurry indicating that an endpoint of the polishing process has been reached (similar to the embodiment discussed above with reference to FIG. 6). Upon determining that such property is reached, the identification system 86 sends a trigger to the control circuitry 40 along the path 73. The control circuitry 40 is configured to stop the polishing process based on receiving the trigger from the identification system 86.

Figure 9:
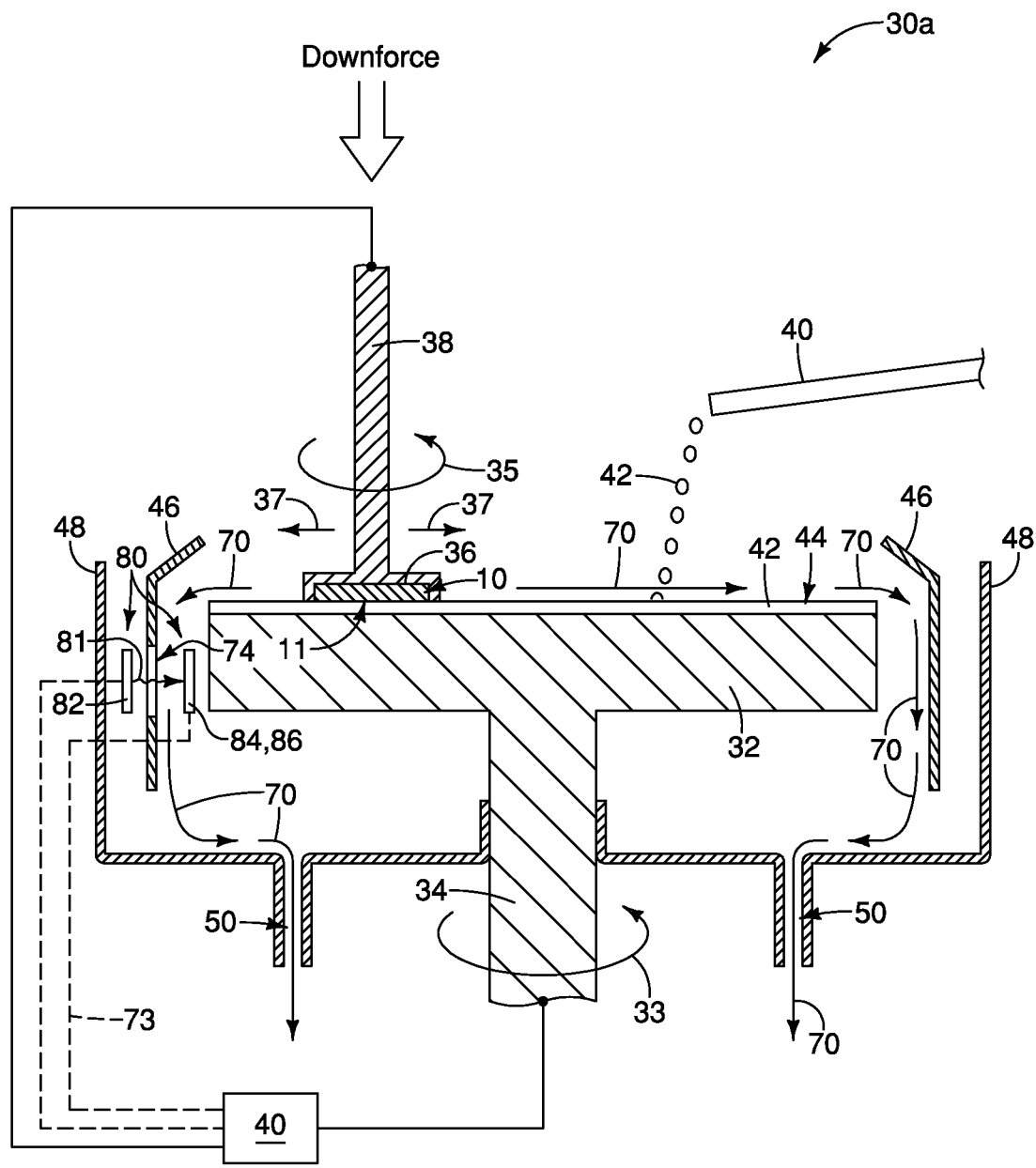
FIG. 9 is a diagrammatic cross-sectional side view of an example embodiment polishing apparatus.

Referring to FIG. 9, an example embodiment is shown in which spectroscopic analysis of the used slurry 70 is conducted at the location 74 along the shield 46 utilizing the spectroscopic device 80 and the window 92. The device 80 of FIG. 9 includes the emitter 82 configured to direct the electromagnetic radiation 81 through the window 92 and through the used slurry 70; and includes the detector 84 which detects electromagnetic radiation 81 which has passed through the used slurry 70. The detector 84 may determine transmittance (or conversely, absorbance) of the used slurry 70 relative to the electromagnetic radiation 81. The device 80 includes the identification system 86 coupled with the detector 84 and configured to identify the property of the used slurry indicating that an endpoint of the polishing process has been reached. Upon determining that such property is reached, the identification system 86 sends a trigger to the control circuitry 40 along the path 73. The control circuitry 40 is configured to stop the polishing process based on receiving the trigger from the identification system 86.

Figure 9A:
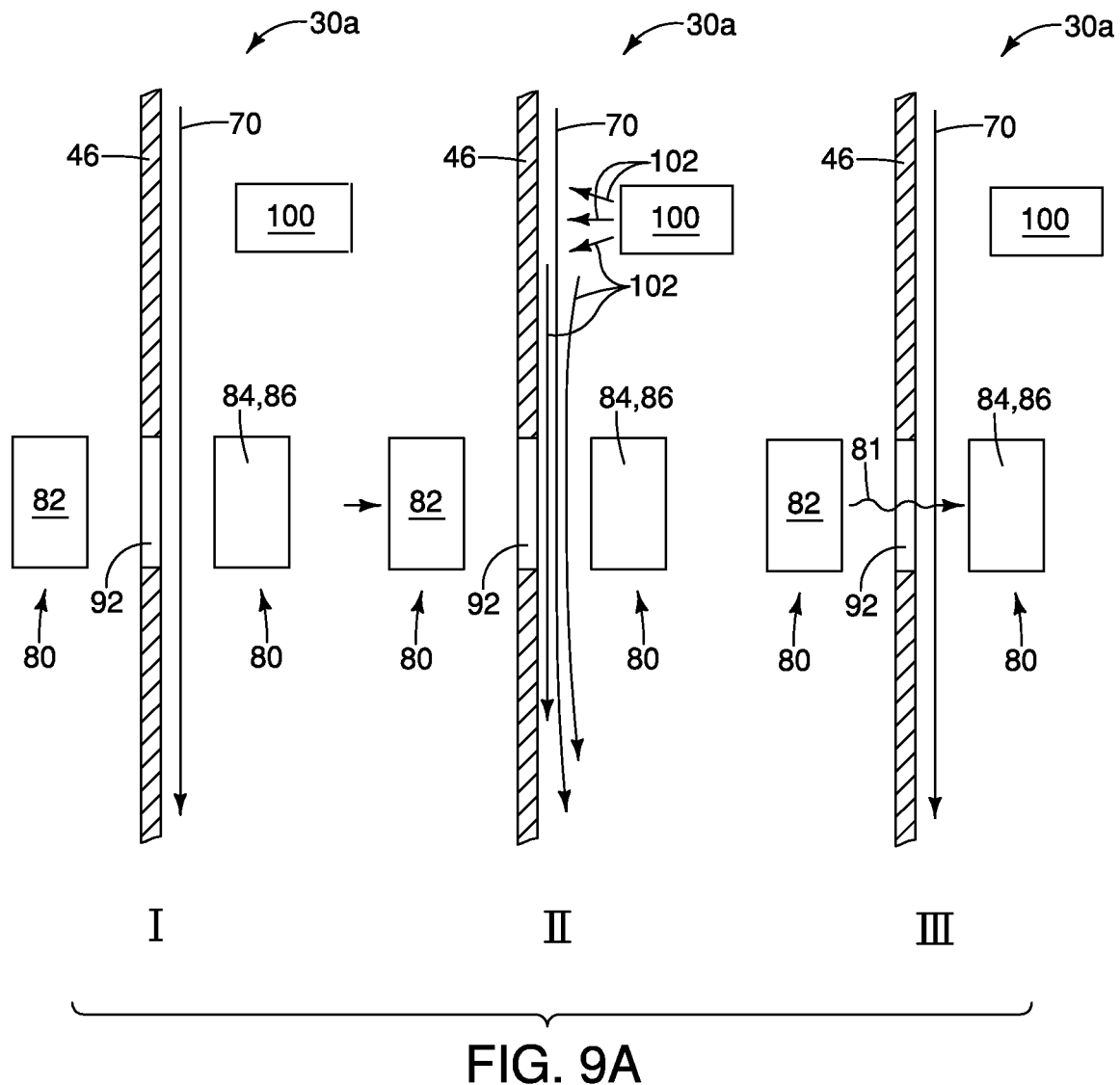
FIG. 9A is a diagrammatic cross-sectional side view of a region of the example embodiment polishing apparatus of FIG. 9 shown in three example operational modes.

In some embodiments, it may be desirable to rinse the window 92 prior to spectroscopic analysis of the used slurry 70. In some embodiments, an operator will have sufficient experience with a polishing process to know an approximate duration required to reach the endpoint. The window 92 may be rinsed after a substantial duration of the polishing process, and shortly before the endpoint of the polishing process is expected. FIG. 9A shows an expanded region of construction 30a in accordance with an embodiment in which a nozzle 100 is provided adjacent shield 46 and utilized to rinse the window 92. In a first operational mode, I, the used slurry 70 flows across the window 92. In a second operational mode, II, cleaning fluid 102 (e.g., deionized water) is expelled from nozzle 100 and flushed across the window 92 to rinse the window. In the illustrated embodiment, the used slurry 70 continues to flow across the window 92 as the window is rinsed with the cleaning fluid 102. In a third operational mode, III, the flow of cleaning fluid 102 is stopped, and the electromagnetic radiation 81 is passed through the window 92 and the used slurry 70 so that the used slurry may be monitored to ascertain when the endpoint of the polishing process is reached. The flow of cleaning fluid from nozzle 100 may be controlled with the controller 40 shown in FIG. 9. In some embodiments, the nozzle 100 may be considered to be part of a spray mechanism controlled with the controller 40.

Although the rinsing of window 92 is described with reference to FIG. 9, in other embodiments analogous rinsing may be utilized relative to one or more of the embodiments described above with reference to FIG. 7, FIG. 7A and FIG. 8.

Figure 10:
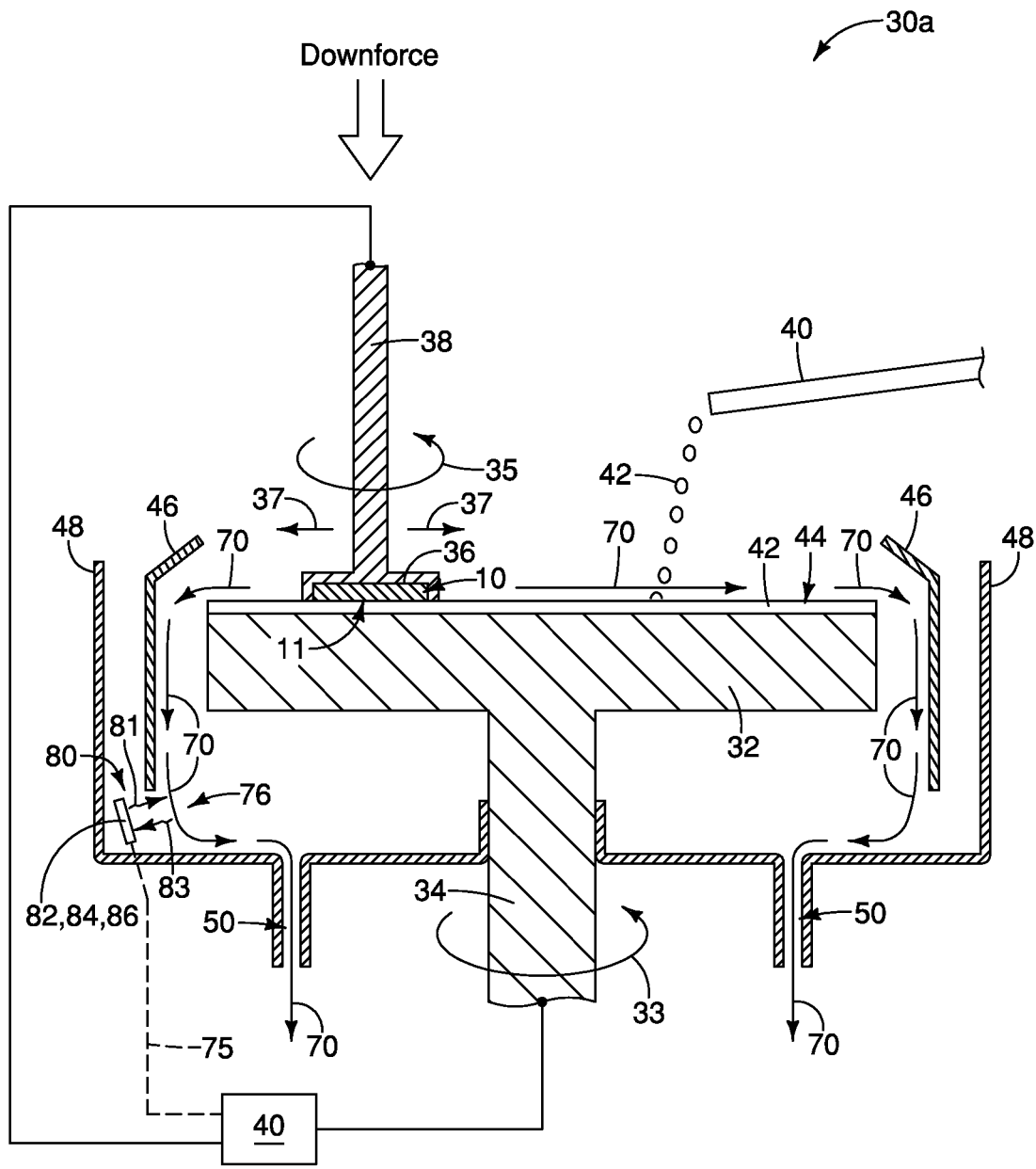
FIG. 10 is a diagrammatic cross-sectional side view of an example embodiment polishing apparatus.

Referring to FIG. 10, an example embodiment is shown in which spectroscopic analysis of the used slurry 70 is conducted at the location 76 as the used slurry 70 falls from the shield 46 toward the basin 48. The spectroscopic analysis utilizes the spectroscopic device 80, and in the shown embodiment involves emission of first electromagnetic radiation 81 toward the used slurry, and detection of second electromagnetic radiation 83 reflected from the used slurry. The device 80 includes the identification system 86 coupled with the detector 84 and configured to identify the property of the used slurry indicating that an endpoint of the polishing process has been reached. Upon determining that such property is reached, the identification system 86 sends a trigger to the control circuitry 40 along the path 75. The control circuitry 40 is configured to stop the polishing process based on receiving the trigger from the identification system 86.

Figure 11:
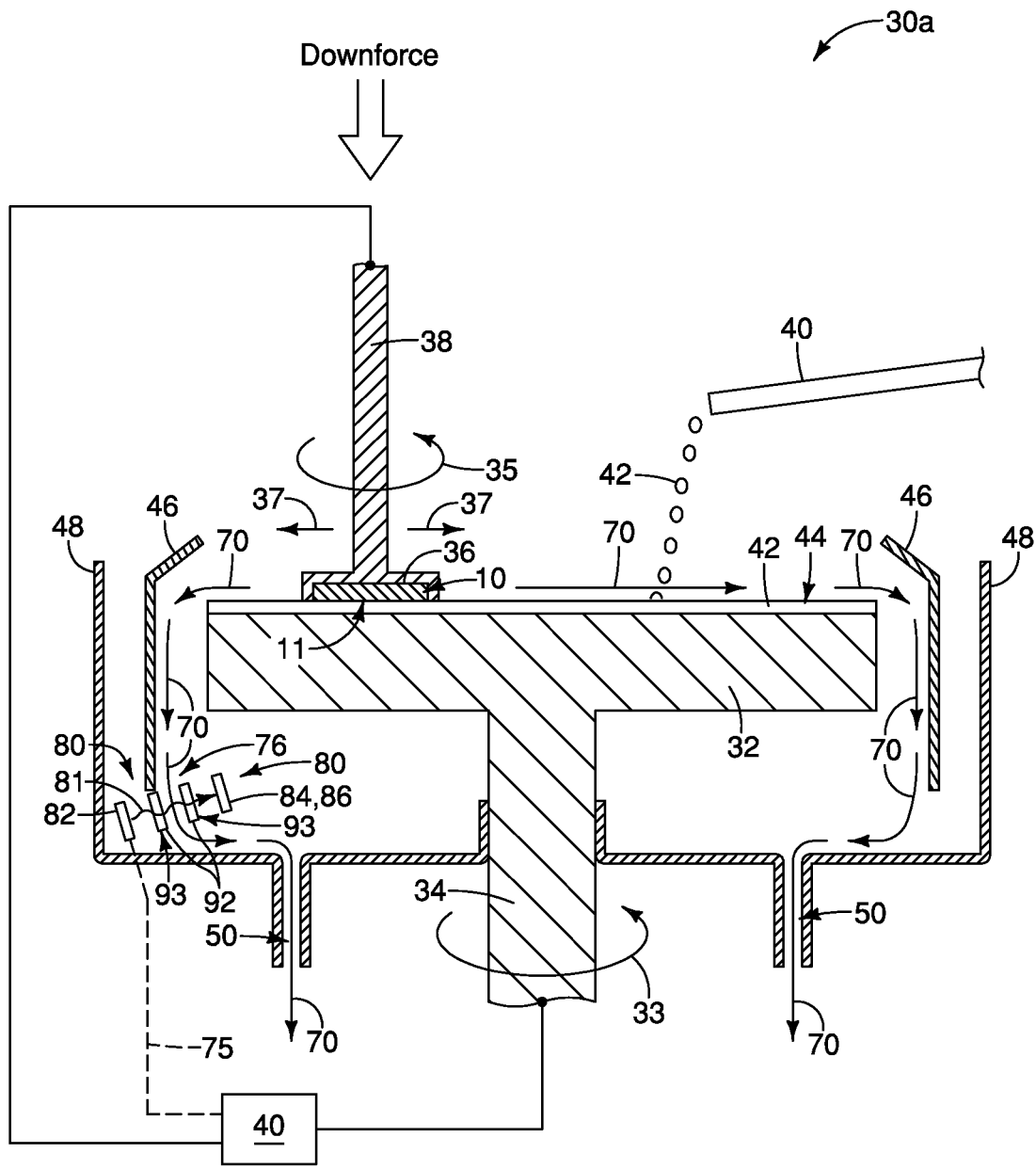
FIG. 11 is a diagrammatic cross-sectional side view of an example embodiment polishing apparatus.

Referring to FIG. 11, an example embodiment is shown in which spectroscopic analysis of the used slurry 70 is conducted at the location 76 beneath the shield 46 utilizing the spectroscopic device 80 and a conduit 93 having a transparent window 92. The device 80 of FIG. 11 includes the emitter 82 configured to direct the electromagnetic radiation 81 through the window 92 and through the used slurry 70; and includes the detector 84 which detects electromagnetic radiation 81 which has passed through the used slurry 70. The detector 84 may determine transmittance (or conversely, absorbance) of the used slurry 70 relative to the electromagnetic radiation 81. The device 80 includes the identification system 86 coupled with the detector 84 and configured to identify the property of the used slurry indicating that an endpoint of the polishing process has been reached. Upon determining that such property is reached, the identification system 86 sends a trigger to the control circuitry 40 along the path 75. The control circuitry 40 is configured to stop the polishing process based on receiving the trigger from the identification system 86.

The conduit 93 of FIG. 11 contains the used slurry 70 and may be utilized to concentrate the used slurry 70 into a location in front of the emitter 82 of the spectroscopic device 80. Such may be advantageous in some embodiments. In other embodiments, the conduit 93 of FIG. 11 may be omitted and the electromagnetic radiation 81 may be passed through the used slurry 70 as it falls in an uncontained manner from the shield 46 to the basin 48 (analogous to the embodiment described above with reference to FIG. 10; although, in some embodiments a conduit 93 of the type shown in FIG. 11 may be utilized in applications of the type described above with reference to FIG. 10).

Figure 11A:
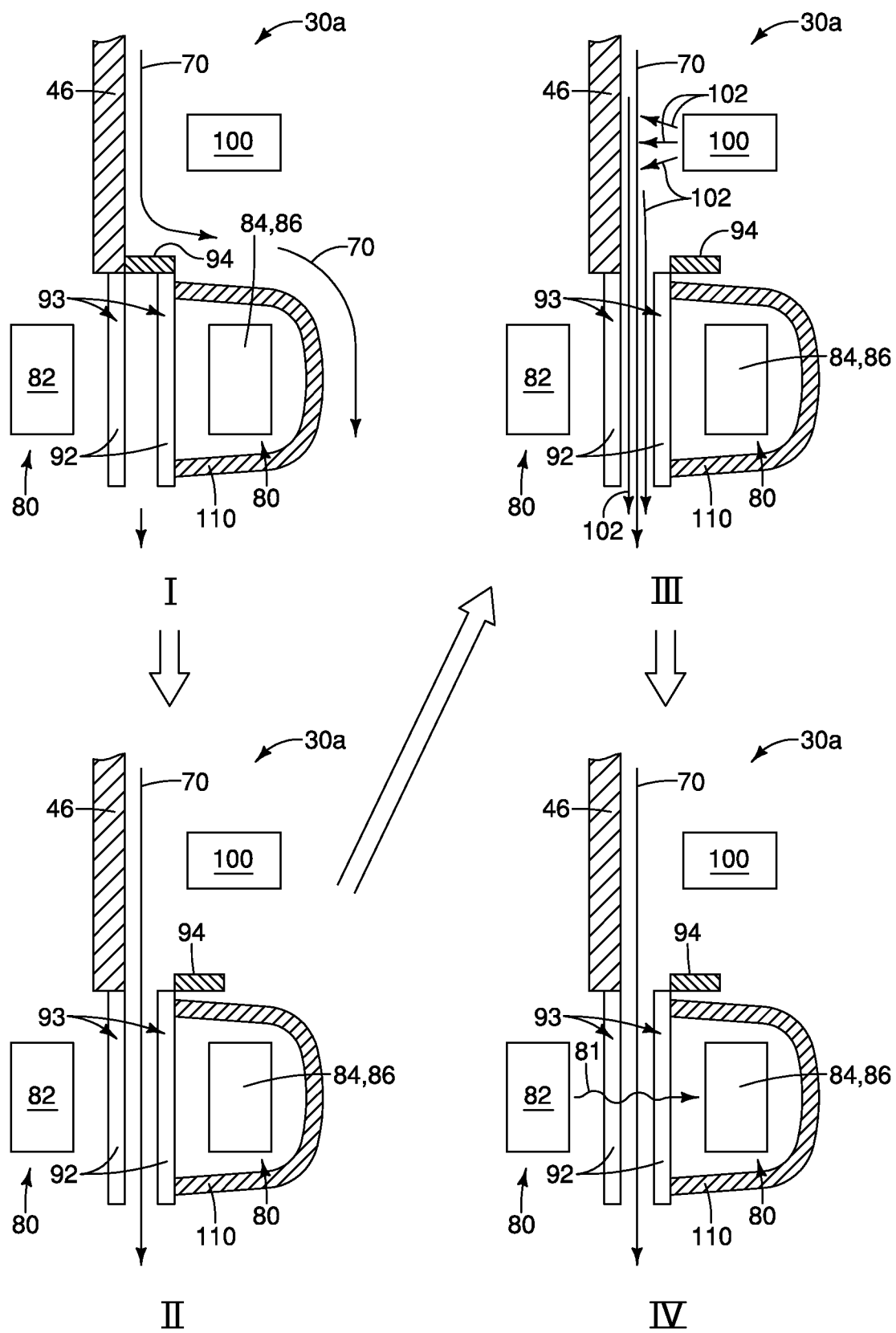
FIG. 11A is a diagrammatic cross-sectional side view of a region of the example embodiment polishing apparatus of FIG. 11 shown in four example operational modes.

If the conduit 93 is utilized, such may be gated in a manner analogous to that described above with reference to FIG. 7A, and the interior of the conduit may be rinsed in a matter analogous to the window rinsing described above with reference to FIG. 9A. For instance, FIG. 11A shows an expanded region of construction 30a in accordance with an embodiment in which a gate 94 is provided operatively adjacent an opening into the conduit 93, and in which a nozzle 100 is provided over the conduit 93. In a first operational mode, I, the gate 94 blocks the inlet of conduit 93 (i.e., is in a "closed" position), and accordingly the used slurry 70 does not flow into the conduit. Instead, the used slurry 70 flows around the conduit, and in the shown embodiment flows around the detection/identification component (84,86) of spectroscopic device 80. An optional housing 110 may be provided around the detection/identification component (84,86) to protect such component from exposure to the used slurry 70. In a second operational mode, II, the gate 94 has been moved to an "open" position to enable used slurry 70 to flow within the conduit 93 and across the window 92. In a third operational mode, III, cleaning fluid 102 (e.g., deionized water) is expelled from nozzle 100 and flushed into the conduit 93 and across the window 92 to rinse the window. In the illustrated embodiment, the used slurry 70 continues to flow across the window 92 as the window is rinsed with the cleaning fluid 102. In a fourth operational mode, IV, the flow of cleaning fluid 102 is stopped, and the electromagnetic radiation 81 is passed through the window 92 and the used slurry 70 so that the used slurry may be monitored to ascertain when the endpoint of the polishing process is reached. The movement of gate 94 and the flow of cleaning fluid from nozzle 100 may be controlled with the controller 40 shown in FIG. 11.

Although the gate 94 is opened before the rinse fluid 102 is sprayed along shield 46 in the shown embodiment, in other embodiments the gate 94 may be opened after the flow of the rinse fluid 102 is started, or simultaneously with the start of the flow of the rinse fluid 102.

In some embodiments, the gate 94 may be utilized to block passage of the used slurry 70 through the conduit 93 for a first period during a duration of a polishing process before the endpoint of the polishing process is expected, and then the gate may be opened to enable passage of the used slurry 70 through the conduit 93 for a second period which encompasses a time that the endpoint of the polishing is expected. The rinsing of the conduit with the cleaning fluid 102 may be conducted during the second period and before the time that the endpoint of the polishing process is expected. Such may enable the window 92 to be kept relatively clean in order to obtain better signal-to-noise during spectroscopic analysis of the used slurry than would be achieved with a dirty window 92.

Although the embodiment described above with reference to FIG. 7A used the gate 94 in the absence of the rinse fluid 102, in other applications such embodiment could use the rinse fluid 102 in combination with a gate analogously to the embodiment described with reference to FIG. 11A. Also, in some applications embodiments analogous to that of FIG. 11A may utilize the gate 94 alone, rather than the gate in combination with the rinse fluid 102. Also, in some applications embodiments analogous to those of FIGS. 7A and 11A may be utilized with rinse fluid 102 alone, instead of with rinse fluid in combination with the gate 94.

The CMP processing described herein may be applied to fabrication of a diverse range of semiconductor devices. For instance, the CMP processing may be utilized during fabrication of memory, logic, sensors, etc. In some applications, the CMP processing may be utilized during fabrication of three-dimensional memory; such as, for example, three-dimensional cross-point architecture, three-dimensional NAND, etc.

The particular orientation of the various embodiments in the drawings is for illustrative purposes only, and the embodiments may be rotated relative to the shown orientations in some applications. The description provided herein, and the claims that follow, pertain to any structures that have the described relationships between various features, regardless of whether the structures are in the particular orientation of the drawings, or are rotated relative to such orientation.

The cross-sectional views of the accompanying illustrations only show features within the planes of the cross-sections, and do not show materials behind the planes of the cross-sections, unless indicated otherwise, in order to simplify the drawings.

When a structure is referred to above as being "on" or "against" another structure, it can be directly on the other structure or intervening structures may also be present. In contrast, when a structure is referred to as being "directly on" or "directly against" another structure, there are no intervening structures present.

Some embodiments include an apparatus having a polishing mechanism configured to polish a surface of a wafer during a polishing process. The polishing mechanism provides a vertical force on the surface of the wafer of less than or equal to about 1 pound per square inch (psi) during the polishing process. The polishing mechanism converts fresh slurry to used slurry during the polishing process. At least one emitter is configured to direct electromagnetic radiation onto or through the used slurry. At least one detector is configured to detect transmittance of the electromagnetic radiation through the used slurry or reflection of the electromagnetic radiation from the used slurry. An identification system is coupled with the at least one detector and is configured to identify a property of the used slurry indicating that an endpoint of the polishing process has been reached; and is configured to send a trigger upon identifying the property of the used slurry. Control circuitry is coupled with the identification system and is configured to stop the polishing process based on receiving the trigger from the identification system.

Some embodiments include an apparatus which comprises a platen having an upper surface configured to spin during a polishing process. A wafer holder is configured to retain a wafer and to press the wafer toward the upper surface of the platen during the polishing process. The wafer holder is configured to spin the wafer relative to the upper surface of the platen during the polishing process, and is configured to sweep the wafer laterally across the upper surface of the platen during the polishing process. The wafer is pressed toward the upper surface of the platen with a downward force of less than or equal to about 1 pound per square inch (psi) during the polishing process. A slurry-dispensing mechanism is adjacent the upper surface of the platen. A shield surrounds a lateral periphery of the platen and is configured to block laterally expelled used slurry during the polishing process. A basin is beneath the shield and is configured to collect the used slurry blocked by the shield. An outlet in the basin enables the used slurry to exit the basin. An outlet path is downstream of the outlet. The used slurry flows from the basin along the outlet path. At least one emitter is configured to direct electromagnetic radiation onto or through the used slurry as it flows along the upper surface of the platen, along the shield, into the basin and/or along the outlet path. At least one detector is configured to detect transmittance of the electromagnetic radiation through the used slurry or reflection of the electromagnetic radiation from the used slurry. An identification system is coupled with the at least one detector and is configured to identify a property of the used slurry indicating that an endpoint of the polishing process has been reached; and is configured to send a trigger upon identifying the property of the used slurry. Control circuitry is coupled with the identification system and is configured to stop the polishing process based on receiving the trigger from the identification system.

Some embodiments include a polishing method which comprises pressing a wafer toward an upper surface of a platen while moving the wafer laterally relative to the upper surface of the platen, and passing polishing slurry between the wafer and the upper surface of the platen as the wafer is moved during a polishing process. The slurry becomes used slurry as the slurry passes between the wafer and the upper surface of the platen. The wafer loses material into the used slurry. The wafer is pressed toward the upper surface of the platen with a downward force of less than or equal to about 1 pound per square inch (psi). Emitted electromagnetic radiation is directed onto or through the used slurry as the used slurry flows away from the wafer. A detector is utilized to detect transmittance of the electromagnetic radiation through the used slurry or reflection of the electromagnetic radiation from the used slurry. An electronic identification system is coupled with the detector and is utilized to identify a property of the used slurry indicating that an endpoint of the polishing process has been reached. The electronic identification system sends a trigger to control circuitry upon identifying the property of the used slurry. The control circuitry stops the polishing process based on receiving the trigger.

In compliance with the statute, the subject matter disclosed herein has been described in language more or less specific as to structural and methodical features. It is to be understood, however, that the claims are not limited to the specific features shown and described, since the means herein disclosed comprise example embodiments. The claims are thus to be afforded full scope as literally worded, and to be appropriately interpreted in accordance with the doctrine of equivalents.

We claim:

1. A polishing method comprising:
   pressing a wafer toward an upper surface of a platen while moving the wafer laterally relative to the upper surface of the platen, and passing polishing slurry between the wafer and the upper surface of the platen as the wafer is moved during a polishing process, the wafer having a surface area; the slurry becoming used slurry as the slurry passes between the wafer and the upper surface of the platen; the wafer losing material into the used slurry; the wafer being pressed toward the upper surface of the platen with a downward force of less than or equal to about 1 pound per square inch (psi);
   directing emitted electromagnetic radiation onto or through the used slurry while the used slurry is outside the surface area as the used slurry flows away from the wafer;
   utilizing a detector to detect transmittance of the electromagnetic radiation through the used slurry or reflection of the electromagnetic radiation from the used slurry;
   utilizing an electronic identification system coupled with the detector to identify a property of the used slurry indicating that an endpoint of the polishing process has been reached;
   the electronic identification system sending a trigger to control circuitry upon identifying the property of the used slurry; and
   the control circuitry stopping the polishing process based on receiving the trigger.

2. The polishing method of claim 1 wherein the property is the presence of a constituent within the used slurry.

3. The polishing method of claim 1 wherein the property is the presence of carbon within the used slurry.

4. The polishing method of claim 1 wherein the emitted electromagnetic radiation is passed through a window toward the used slurry.

5. The polishing method of claim 4 wherein the endpoint of the polishing process is expected after the polishing process has been conducted for a duration; and including rinsing the window with cleaning fluid at some time during the duration and before the endpoint of the polishing process is expected.

6. The polishing method of claim 1 wherein the used slurry is flowed through a conduit, and wherein the emitted electromagnetic radiation is directed through conduit and the used slurry as the used slurry is flowing through the conduit.

7. The polishing method of claim 6 wherein the endpoint of the polishing process is expected after the polishing process has been conducted for a duration; and including rinsing the conduit with cleaning fluid at some time during the duration and before the endpoint of the polishing process is expected.

8. The polishing method of claim 6 wherein the endpoint of the polishing process is expected after the polishing process has been conducted for a duration; and including blocking passage of the used slurry through the conduit for a first period during the duration and before the endpoint of the polishing process is expected, and enabling passage of the used slurry through the conduit for a second period which encompasses a time that the endpoint of the polishing process is expected.

9. The polishing method of claim 6 wherein the endpoint of the polishing process is expected after the polishing process has been conducted for a duration, and including:
   blocking passage of the used slurry through the conduit for a first period during the duration and before the endpoint of the polishing process is expected, and enabling passage of the used slurry through the conduit for a second period which encompasses a time that the endpoint of the polishing process is expected; and
   rinsing the conduit with cleaning fluid during the second period and before the time that the endpoint of the polishing process is expected.

10. A polishing method comprising:
    providing a polishing device having a platen comprising an upper surface;
    providing a wafer comprising a surface having a surface area;
    providing a vertical force on the surface of the wafer of less than or equal to about one pound per square inch during the polishing;
    during the providing the vertical force, converting a fresh slurry to used slurry;
    directing electromagnetic radiation onto or through the used slurry outside the surface area; and
    detecting one or both of transmittance of the electromagnetic radiation through the used slurry and reflection of the electromagnetic radiation from the used slurry.

11. The method of claim 10 wherein the detecting is performed by a detector coupled to an identification system, the method further comprising utilizing the identification system to identify a property of the used slurry to identify an endpoint of the polishing and sending a trigger upon identifying the property.

12. The method of claim 11 wherein the property is a presence of a constituent within the used slurry.

13. The method of claim 11 wherein the property is a presence of carbon within the used slurry.

14. The method of claim 11 wherein the property is a threshold concentration of a constituent within the used slurry.

15. The method of claim 11 wherein the property is a threshold concentration of carbon within the used slurry.

16. The method of claim 11 further comprising providing control circuitry coupled with the identification system, and upon receipt of the trigger by the identification system, ceasing the polishing process utilizing the control circuitry.

17. The method of claim 10 further comprising moving the wafer laterally relative to the upper surface of the platen during the providing vertical force, and passing the fresh polishing slurry between the wafer and the upper surface of the platen as the wafer is moved laterally.

18. The polishing method of claim 10 wherein the emitted electromagnetic radiation is passed through a window toward the used slurry.

19. The polishing method of claim 17 wherein the endpoint of the polishing process is expected after the polishing process has been conducted for a duration; and including rinsing the window with cleaning fluid at some time during the duration and before the endpoint of the polishing process is expected.

20. The polishing method of claim 10 wherein the used slurry is flowed through a conduit, and wherein the emitted electromagnetic radiation is directed through conduit and the used slurry as the used slurry is flowing through the conduit.

* * * * *